United States Patent [19]

Chandrasegaran

[11] Patent Number: 5,356,802
[45] Date of Patent: Oct. 18, 1994

[54] FUNCTIONAL DOMAINS IN FLAVOBACTERIUM OKEANOKOITES (FOKI) RESTRICTION ENDONUCLEASE

[75] Inventor: Srinivasan Chandrasegaran, Baltimore, Md.

[73] Assignee: The Johns Hopkins University, Baltimore, Md.

[21] Appl. No.: 862,831

[22] Filed: Apr. 3, 1992

[51] Int. Cl.$^5$ .................. C12N 9/22; C12N 15/55; C12N 15/62

[52] U.S. Cl. .................. 435/199; 536/23.2; 536/23.4

[58] Field of Search .................. 435/199, 193; 935/47; 536/23.2, 23.4

[56] References Cited

PUBLICATIONS

Bocklage, H., et al, (1991) Nuc. Acids Res 19(5), 1007–1013.

Kita, K., et al, (1989) J. Biol. Chem. 264(10), 5751–5756.

Looney, M. C., et al, (1989) Gene 80, 193–208.

Li, L., et al (1992) Proc. Natl. Acad. Sci., USA 89, 4275–4279.

*Primary Examiner*—Charles L. Patterson, Jr.
*Attorney, Agent, or Firm*—Cushman, Darby & Cushman

[57] ABSTRACT

The present inventor have identified of the recognition and cleavage domains of the FokI restriction endonuclease. Accordingly, the present invention relates to DNA segments encoding the recognition and cleavage domains of the FokI restriction endonuclease, respectively. The 41 kDa N-terminal fragment constitutes the FokI recognition domain while the 25 kDa C-terminal fragment constitutes the FokI cleavage nuclease domain. The present invention also relates to hybrid restriction enzymes comprising the nuclease domain of the FokI restriction endonuclease linked to a recognition domain of another enzyme.

6 Claims, 9 Drawing Sheets

Fig. 1

FokIM

5' primer

```
        NcoI            7-bp spacer
5' TA  CCATGG AGGT   TTAAAAT  ATG AGA TTT ATT GGC AGC
            RBS                Met Arg Phe Ile Gly Ser
```

3' primer

```
        18-bp complement         NcoI
3' ACT ACG ACA CAG TAA ATT AAG  GGTACC  ATA 5'
```

FokIR

5' primer

```
        BamHI     RBS    7-bp spacer
5' TA  GGATCC  GGAGGT  TTAAAAT  ATG GTT TCT AAA ATA AGA ACT
                                 Met Val Ser Lys Ile Arg Thr
```

3' primer

```
       Complementary Strand                    BamHI
3' TTA TTG CCG CTC TAT  TTG AAA  ATT  ACT  CC TAGG  AT 5'
   Asn Asn Gly Glu Ile  Asn Phe
```

FUNCTIONAL DOMAINS IN FLAVOBACTERIUM OKEANOKOITES (FOKI) RESTRICTION ENDONUCLEASE

BACKGROUND OF THE INVENTION

1. Field of the Invention

The present invention relates to the FokI restriction endonuclease system. In particular, the present invention relates to DNA segments encoding the separate functional domains of this restriction endonuclease system.

2. Background Information

Type II endonucleases and modification methylases are bacterial enzymes that recognize specific sequences in duplex DNA. The endonuclease cleaves the DNA while the methylases methylates adenine or cytosine residues so as to protect the host-genome against cleavage [Type II restriction and modification enzymes. In Nucleases (Eds. Modrich and Roberts) Cold Spring Harbor Laboratory. New York, pp. 109-154, 1982]. These restriction-modification (R-M) systems function to protect cells from infection by phage and plasmid molecules that would otherwise destroy them.

As many as 2500 restriction enzymes with over 200 specificities have been detected and purified (Wilson and Murray, Annu. Rev. Genet. 25:585-627, 1991). The recognition sites of most of these enzymes are 4-6 base pairs long. The small size of the recognition sites is beneficial as the phage genomes are usually small and these small recognition sites occur more frequently in the phage.

Eighty different R-M systems belonging to the Type IIS class with over 35 specificities have been identified. This class is unique in that the cleavage site of the enzyme is separate from the recognition sequence. Usually the distance between the recognition site and the cleavage site is quite precise (Szybalski et al., Gene, 100:13-26, 1991). Among all these enzymes, the FokI restriction endonuclease is the most well characterized member of the Type IIS class. The FokI endonuclease (RFokI) recognizes asymmetric pentanucleotides in double-stranded DNA, 5' GGATG-3' (SEQ ID NO: 1) in one strand and 3'-CCTAC-5' (SEQ ID NO: 2) in the other, and introduces staggered cleavages at sites downstream from the recognition site (Sugisaki et al., Gene 16:73-78; 1981). In contrast, the FokI methylase (MFokI) modifies DNA thereby rendering the DNA resistant to digestion by FokI endonuclease. The FokI restriction and modification genes have been cloned and their nucleotide sequences deduced (Kita et al., J. of Biol. Chem., 264:575-5756, 1989). Nevertheless, the domain structure of the FokI restriction endonuclease remains unknown, although a three domain structure has been suggested (Wilson and Murray, Annu. Rev. Genet. 25:585-627, 1991).

SUMMARY OF THE INVENTION

Accordingly, it is an object of the present invention to provide isolated domains of Type IIS restriction endonuclease.

It is another object of the present invention to provide hybrid restriction enzymes which are useful for mapping and sequencing.

Various other objects and advantages of the present invention will become obvious from the drawings and the following description of the invention.

In one embodiment, the present invention relates to a DNA segment encoding the N-terminus of a Type IIS endonuclease which contains the sequence-specific recognition activity of the Type IIS endonuclease or a DNA segment encoding the C-terminus of a Type IIS endonuclease which contains the cleavage activity of the Type IIS endonuclease.

In another embodiment, the present invention relates to an isolated protein consisting essentially of the N-terminus of the FokI restriction endonuclease which protein has the sequence-specific recognition activity of the endonuclease or an isolated protein consisting essentially of the C-terminus of the FokI restriction endonuclease which protein has the nuclease activity of the endonuclease.

In a further embodiment, the present invention relates to a DNA construct comprising a first DNA segment encoding the C-terminus of a Type IIS endonuclease which contains the cleavage activity of the Type IIS endonuclease; a second DNA segment encoding a sequence specific recognition domain other than the recognition domain of the Type IIS endonuclease; and a vector. In the construct, the first DNA segment and the second DNA segment are operably linked to the vector to result in the production of a hybrid restriction enzyme.

In another embodiment, the present invention relates to a hybrid restriction enzyme comprising the C-terminus of a Type IIS endonuclease which contains the cleavage activity of the Type IIS endonuclease linked to a recognition domain of an enzyme or a protein other than the Type IIS endonuclease from which the cleavage domain is obtained.

BRIEF DESCRIPTION OF THE DRAWINGS

FIG. 1 shows sequences of the 5' and 3' primers used to introduce new translation signals into fokIM and fokIR genes during PCR amplification. (SEQ ID NOs: 3-9). SD represents Shine-Dalgarno consensus RBS for Escherichia coli (E. coli) and 7-bp spacer separates the RBS from the ATG start condon. The fokIM primers are flanked by NcoI sites. The fokIR primers are flanked by BamHI sites. Start and stop codons are shown in bold letters. The 18-bp complement sequence is complementary to the sequence immediately following the stop codon of MfokI gene.

GAGAGCATCCAGAGG-3′(SEQ ID NO:11). Lanes: 1, protein standards; 2, FokI endonuclease; 3, 2.5 min; 4, 5 min; 5, 10 min; 6, 20 min; 7, 40 min; 8, 80 min; 9, 160 min of trypsin digestion respectively. Lanes 10–13: HPLC purified tryptic fragments. Lanes: 10, 41 kDa fragment; 11, 30 kDa fragment; 12, 11 kDa fragment; and 13, 25 kDa fragment.

Figure 5:
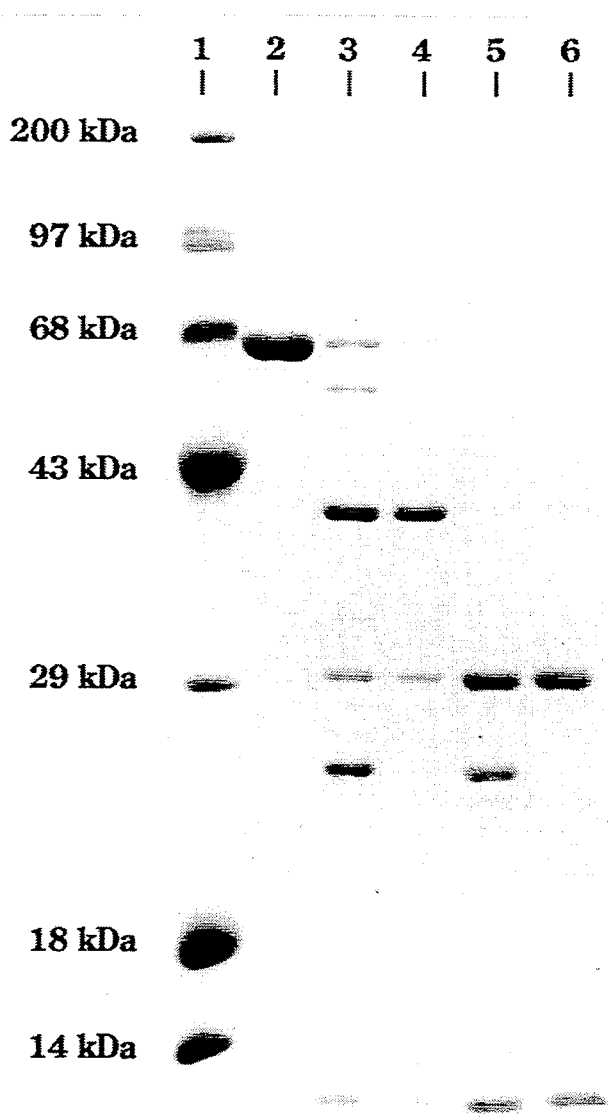

FIG. 5 shows the identification of DNA binding tryptic fragments of FokI endonuclease using an oligo dT-cellulose column. Lanes: 1, protein standards, 2, FokI endonuclease; 3, 10 min trypsin digestion mixture of FokI-oligo complex; 4, tryptic fragments that bound to the oligo dT-cellulose column; 5, 160 min trypsin digestion mixture of FokI-oligo complex; 6, tryptic fragments that bound to the oligo dT-cellulose column.

Figure 6B:
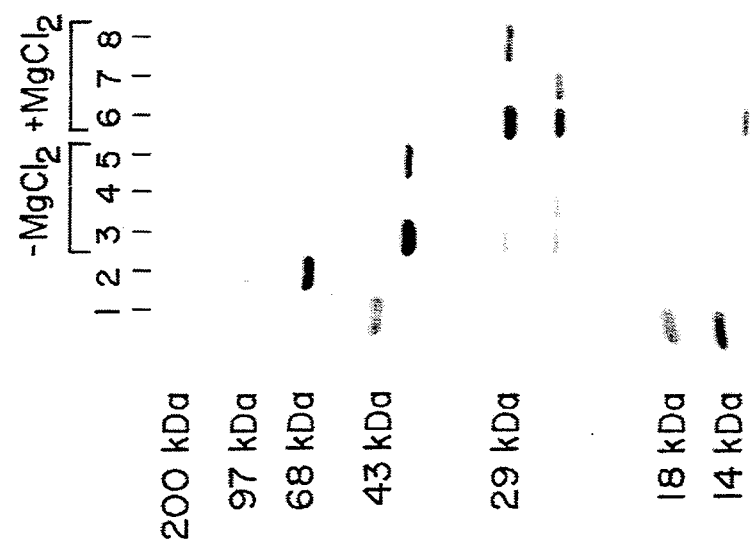
Figure 6A:
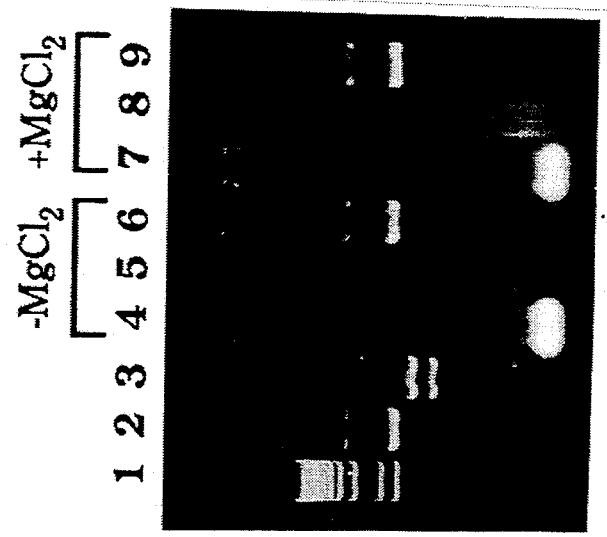

FIG. 6 shows an analysis of the cleavage properties of the tryptic fragments of FokI endonuclease.

(A) The cleavage properties of the tryptic fragments were analyzed by agarose gel electrophoresis. 1 μg of pTZ19R in 10 mM Tris.HCl (pH 8), 50 mM NaCl, 1 mM DTT, and 10 mM $MgCl_2$ was digested with 2 μl of the solution containing the fragments (tryptic digests, breakthrough and eluate respectively) at 37° C. for 1 hr in a reaction volume of 10 μl. Lanes 4 to 6 correspond to trypsin digestion of Fok I-oligo complex in absence of $MgCl_2$. Lanes 7 to 9 correspond to trypsin digestion of FokI-oligo complex in presence of 10 mM $MgCl_2$. Lanes: 1, 1 kb ladder; 2, pTZ19R; 3, pTZ19R digested with FokI endonuclease; 4 and 6, reaction mixture of the tryptic digests of FokI-oligo complex; 5 and 7, 25 kDa C-terminal fragment in the breakthrough volume; 6 and 9, tryptic fragments of FokI that bound to the DEAE column. The intense bands at bottom of the gel correspond to excess oligonucleotides.

(B) SDS (0.1%)-polyacrylamide (12%) gel electrophoretic profiles of fragments from the DEAE column. Lanes 3 to 5 correspond to trypsin digestion of FokI-oligo complex in absence of $MgCl_2$. Lanes 6 to 8 correspond to trypsin digestion of FokI-oligo complex in presence of 10 mM $MgCl_2$. Lanes: 1, protein standards; 2, FokI endonuclease; 3 and 6, reaction mixture of the tryptic digests of FokI-oligo complex; 4 and 7, 25 kDa C-terminal fragment in the breakthrough volume; 5 and 8, tryptic fragments of FokI that bound to the DEAE column.

Figure 7B:
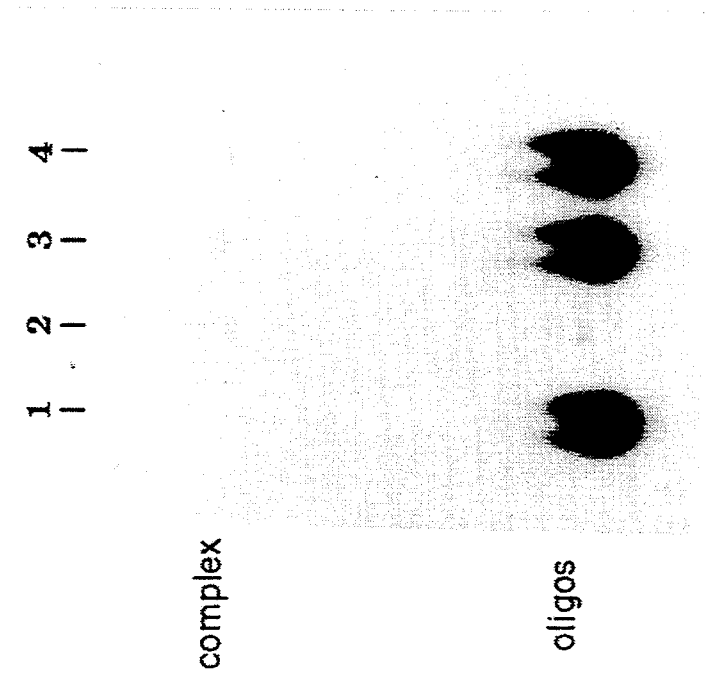
Figure 7A:
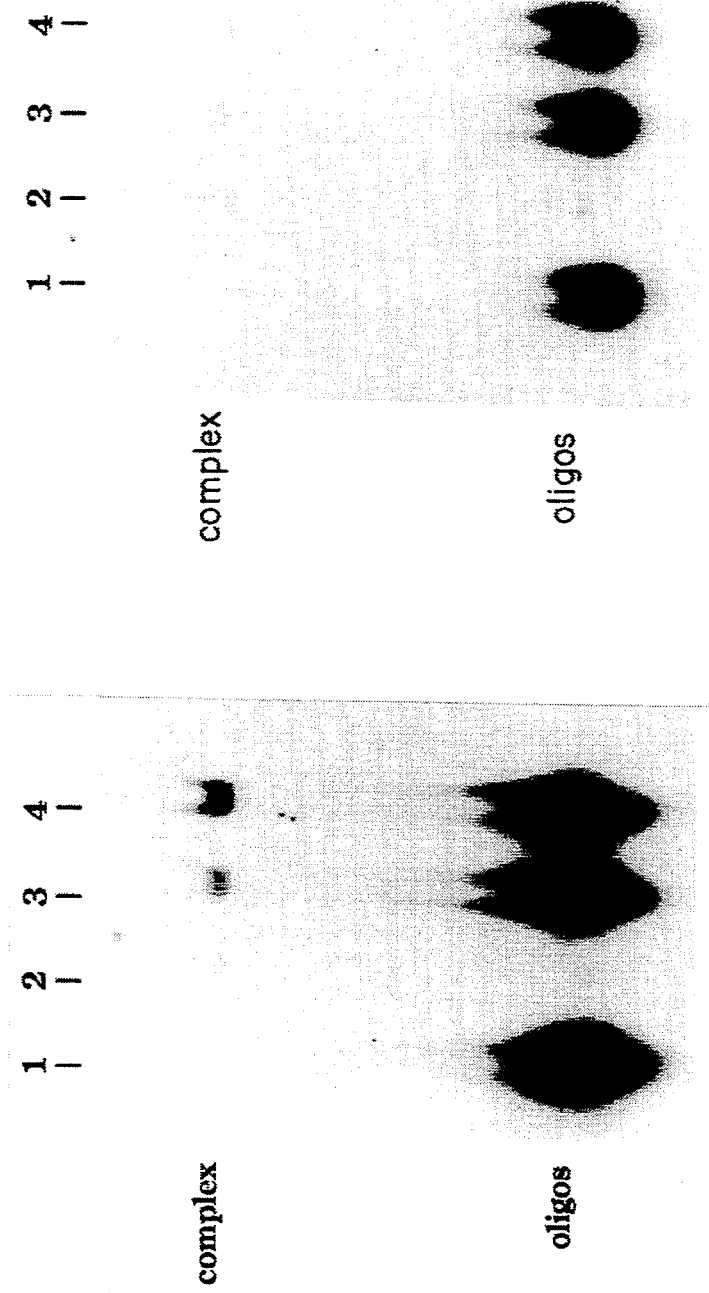

FIG. 7 shows an analysis of sequence-specific binding of DNA by 41 kDa N-terminal fragment using gel mobility shift assays. For the exchange reaction, the complex (10 μl) was incubated with 1 μl of $^{32}P$-labeled specific (or non-specific) oligonucleotide duplex in a volume of 20 μl containing 10 mM Tris. HCl, 50 mM NaCl and 10 mM $MgCl_2$ at 37° C. for various times. 1 μl of the 5′-$^{32}P$-labeled specific probe [d-5′-CCTCTGGATGCTCTC-3′(SEQ ID NO: 10): 5′-GAGAGCATCCAGAGG-3′(SEQ ID NO: 11)] contained 12 picomoles of the duplex and ~50×10³ cpm. 1 μl of the 5′-$^{32}P$-labeled non-specific probe [5′-TAATTGATTCTTAA-3′(SEQ ID NO: 12):5′-ATTAAGAATCAATT-3′(SEQ ID NO: 13)] contained 12 picomoles of the duplex and ~25×10³ cpm. (A) Lanes: 1, specific oligonucleotide duplex; 2, 41 kDa N-terminal fragment-oligo complex; 3 and 4, specific probe incubated with the complex for 30 and 120 min respectively. (B) Lanes: 1, non-specific oligonucleotide duplex; 2, 41 kDa N-terminal fragment-oligo complex; 3 and 4 non-specific probe incubated with the complex for 30 and 120 min respectively.

Figure 8:
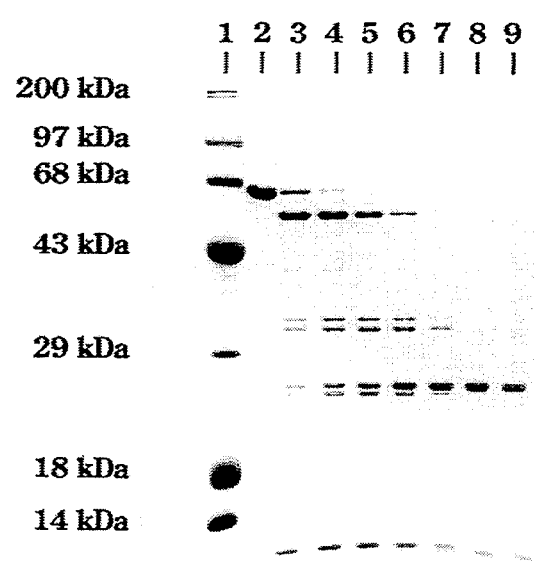

FIG. 8 shows SDS (0.1%) polyacrylamide (12%) gel electrophoretic profiles of tryptic fragments at various time points of trypsin digestion of FokI endonuclease. The enzyme (200 μg) in a final volume of 200 μl containing 10 mM Tris.HCl, 50 mM NaCl and 10 mM $MgCl_2$ was digested with trypsin at RT. The trypsin to FokI ratio was 1:50 by weight. Aliquots (28 μl) from the reaction mixture removed at different time intervals and quenched with excess antipain. Lanes: 1, protein standards; 2, FokI endonuclease; 3, 2.5 min; 4, 5.0 min; 5, 10 min; 6, 20 min; 7, 40 min; 8, 80 min; and 9, 160 min of trypsin digestion respectively.

Figure 9A:
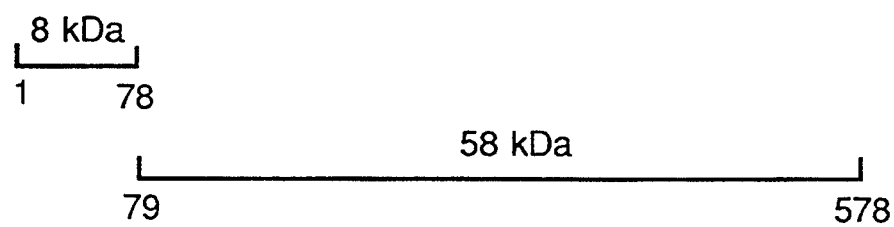
Figure 9B:
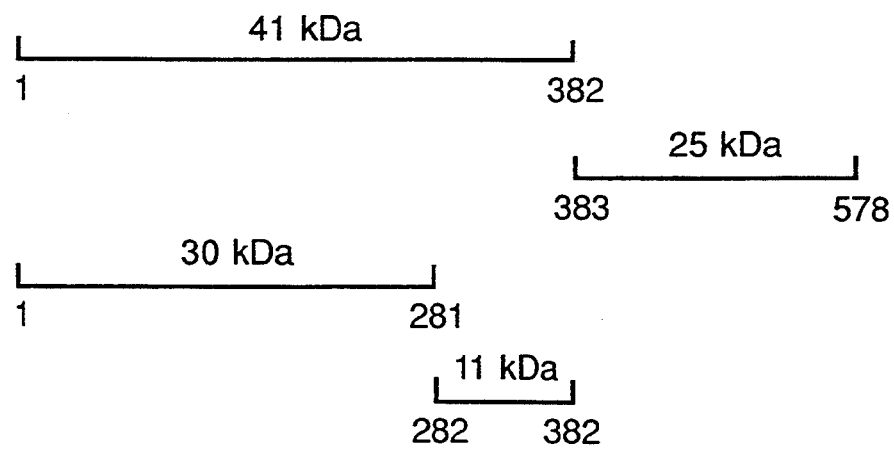

FIG. 9A shows the tryptic map of FokI endonuclease FokI endonuclease fragmentation pattern in absence of the oligonucleotide substrate. FIG. 9B shows the FokI endonuclease fragmentation pattern in presence of the oligonucleotide substrate.

DETAILED DESCRIPTION OF THE INVENTION

The present invention is based on the identification and characterization of the functional domains of the FokI restriction endonuclease. In the experiments resulting in the present invention, it was discovered that the FokI restriction endonuclease is a two domain system, one domain of which possesses the sequence-specific recognition activity while the other domain contains the nuclease cleavage activity.

The FokI restriction endonuclease recognizes the non-palindromic pentanucleotide 5′-GGATG-3′(SEQ ID NO: 1):5′-CATCC-3′(SEQ ID NO: 2) in duplex DNA and cleaves 9/13 nucleotides downstream of the recognition site. Since 10 base pairs are required for one turn of the DNA helix, the present inventors hypothesized that the enzyme would interact with one face of the DNA by binding at one point and cleave at another point on the next turn of the helix. This suggested the presence of two separate protein domains, one for sequence-specific recognition of DNA and one for endonuclease activity. The hypothesized two domain structure was shown to be the correct structure of the FokI endonuclease system by studies that resulted in the present invention.

Accordingly, in one embodiment, the present invention relates to a DNA segment which encodes the N-terminus of the FokI restriction endonuclease (preferably, about the N-terminal ⅔'s of the protein). This DNA segment encodes a protein which has the sequence-specific recognition activity of the endonuclease, that is, the encoded protein recognizes the non-palindromic pentanucleotide d5′-GGATG-3′(SEQ ID NO: 1):5′-CATCC-3′(SEQ ID NO: 2) in duplex DNA. Preferably, the DNA segment of the present invention encodes amino acids 1–382 of the FokI endonuclease.

In a further embodiment, the present invention relates to a DNA segment which encodes the C-terminus of the FokI restriction endonuclease. The protein encoded by this DNA segment of the present invention has the nuclease cleavage activity of the FokI restriction endonuclease. Preferably, the DNA segment of the present invention encodes amino acids 383–578 of the FokI endonuclease. DNA segments of the present invention can be readily isolated from a biological sample using methods known in the art, for example, gel electrophoresis, affinity chromatography, polymerase chain reaction (PCR) or a combination thereof. Further, the DNA segments of the present invention can be chemically synthesized using standard methods in the art.

The present invention also relates to the proteins encoded by the DNA segments of the present invention. Thus, in another embodiment, the present invention relates to a protein consisting essentially of the N-terminus of the FokI endonuclease which retains the sequence-specific recognition activity of the enzyme. This protein of the present invention has a molecular weight of about 41 kilodaltons as determined by SDS polyacrylamide gel electrophoresis in the presence of 2-mercaptoethanol.

In a further embodiment, the present invention relates to a protein consisting essentially of the C-terminus of the FokI restriction endonuclease (preferably, the C-terminal ⅓ of the protein). The molecular weight of this protein is about 25 kilodaltons as determined by SDS polyacrylamide gel electrophoresis in the presence of 2-mercaptoethanol.

The proteins of the present invention can be isolated or purified from a biological sample using methods known in the art. For example, the proteins can be obtained by isolating and cleaving the FokI restriction endonuclease. Alternatively, the proteins of the present invention can be chemically synthesized or produced using recombinant DNA technology and purified.

The DNA segments of the present invention can be used to generate 'hybrid' restriction enzymes by linking other DNA binding protein domains with the nuclease domain of FokI. This can be achieved chemically as well as by recombinant DNA technology. Such chimeric enzymes are useful for physical mapping and sequencing of genomes of various species, such as, humans, mice and plants. For example, such enzymes would be suitable for use in mapping the human genome.

Such chimeric enzymes are also valuable research tools in recombinant DNA technology and molecular biology. Currently only 4–6 base pair cutters and a few 8 base pair cutters are available commercially. (There are about 6 endonucleases which cut >6 base pairs that are available commercially.) By linking other DNA binding proteins to the nuclease domain of FokI, enzymes can be generated that recognize more than 6 base pairs in DNA.

Accordingly, in a further embodiment, the present invention relates to a DNA construct and the hybrid restriction enzyme encoded therein. The DNA construct of the present invention comprises a first DNA segment encoding the nuclease domain of the FokI restriction endonuclease, a second DNA segment encoding a sequence specific recognition domain and a vector. The first DNA segment and the second DNA segment are operably linked to the vector so that expression of the segments can be effected thereby yielding a chimeric restriction enzyme. The construct can comprise regulatory elements such as promoters (for example, T7, tac, trp and lac UV5 promoters), transcriptional terminators or retroregulators (for example, stem loops). Host cells (procaryotes such as *E. coli*) can be transformed with the DNA constructs of the present invention and used for the production of chimeric restriction enzymes.

The hybrid enzymes of the present invention comprise the nuclease domain of FokI linked to a recognition domain of another enzyme or DNA binding protein (such as, naturally occurring DNA binding proteins that recognize >6 base pairs). Suitable recognition domains include, but are not limited to, the recognition domains of zinc finger motifs; homeo domain motifs; other DNA binding protein domains of lambda repressor, lac repressor, cro, gal4; DNA binding protein domains of oncogenes such as myc, jun; and other naturally occurring sequence-specific DNA binding proteins that recognize >6 base pairs.

The hybrid restriction enzymes of the present invention can be produced by those skilled in the art using known methodology. For example, the enzymes can be chemically synthesized or produced using recombinant DNA technology well known in the art. The hybrid enzymes of the present invention can be produced by culturing host cells (such as, HB101, RR1, RB791 and MM294) containing the DNA construct of the present invention and isolating the protein. Further, the hybrid enzymes can be chemically synthesized for example, the linking the nuclease domain of the FokI to the recognition domain using common linkage methods known in the art, for example, using protein crosslinking agents such as EDC/NHS, DSP, etc.

While the FokI restriction endonuclease was the enzyme studied in the following experiments, it is expected that other Type IIS endonucleases (such as, those listed in Table 2) will function using a similar two domain structure which one skilled in the art could readily determine based on the present invention.

The following non-limiting Examples are provided to describe the present invention in greater detail.

EXAMPLES

The following materials and methods were utilized in the isolation and characterization of the FokI restriction endonuclease functional domains as exemplified hereinbelow.

Bacterial strains and plasmids

Recombinant plasmids were transformed into *E.coli* RB791 i$^q$ cells which carry the lac i$^q$ allele on the chromosome (Brent and Ptashne, *PNAS USA*, 78:4204–4208, 1981) or *E.coli* RR1 cells. Plasmid pACYCfokIM is a derivative of pACYC184 carrying the PCR-generated fokIM gene inserted into NcoI site. The plasmid expresses the FokI methylase constitutively and was present in RB791 cells (or RR1 cells) whenever the fokIR gene was introduced on a separate compatible plasmid. The FokI methylase modifies FokI sites and provides protection against chromosomal cleavage. The construction of vectors pRRS and pCB are described elsewhere (Skoglund et al., *Gene*, 88:1–5, 1990).

Enzymes, biochemicals and oligos

Oligo primers for PCR were synthesized with an Applied Biosystem DNA synthesizer using cyanoethyl phosphoramidite chemistry and purified by reversed phase HPLC. Restriction enzymes were purchased from New England Biolabs. The DNA ligase IPTG were from Boehringer-Mannheim. PCR reagents were purchased as a Gene Amp Kit from Perkin-Elmer. Plasmid purification kit was from QIAGEN.

Restriction enzyme assays

Cells from a 5-ml sample of culture medium were harvested by centrifugation, resuspended in 0.5 ml sonication buffer [50 mM Tris.HCl (pH 8), 14 mM 2-mercaptoethanol], and disrupted by sonication (3×5 seconds each) on ice. The cellular debris was centrifuged and the crude extract used in the enzyme assay. Reaction mixtures (10 μl) contained 10 mM Tris.HCl (pH 8), 10 mM MgCl$_2$, 7 mM 2-mercaptoethanol, 50 μg of BSA, 1 μg of plasmid pTZ19R (U.S. biochemicals) and 1 μl of crude enzyme. Incubation was at 37° C. for 15 min. tRNA (10 μg) was added to the reaction mixtures when necessary to inhibit non-specific nucleases. After digestion, 1 μl of dye solution (100 mM EDTA, 0.1% bromophenol blue, 0.1% xylene cyanol, 50% glycerol) was added, and the samples were electrophoresed on a 1% agarose gel. Bands were stained with 0.5 μg ethidium bromide/ml and visualized with 310-nm ultraviolet light.

SDS/PAGE

Proteins were prepared in sample buffer and electrophoresed in SDS (0.1%)polyacrylamide (12%) gels as described by Laemmli (Laemmli, *Nature*, 222:680–685, 1970). Proteins were stained with coomassie blue.

EXAMPLES I

Cloning of FokI RM system

The FokI system was cloned by selecting for the modification phenotype. *Flavobacterium okeanokoites* strain DNA was isolated by the method described by Caserta et al. (Caserta et al., *J. Biol. Chem.*, 262:4770–4777, 1987). Several *Flavobacterium okeanokoites* genome libraries were constructed in plasmids pBR322 and pUC13 using the cloning enzymes PstI, BamHI and BglII. Plasmid library DNA (10 μg) was digested with 100 units of FokI endonuclease to select for plasmids expressing fokIM+ phenotype.

Surviving plasmids were transformed into RR1 cells and transformants were selected on plates containing appropriate antibiotic. After two rounds of biochemical enrichment, several plasmids expressing the fokIM+ phenotype from these libraries were identified. Plasmids from these clones were totally resistant to digestion by FokI.

Among eight transformants that were analyzed from the *F. okeanokoites* pBR322 PstI library, two appeared to carry the fokIM gene and plasmids from these contained a 5.5 kb PstI fragment. Among eight transformants that were picked from *F. okeanokoites* pBR322 BamHI library, two appeared to carry the fokIM gene and their plasmids contained ~18 kb BamHI fragment. Among eight transformants that were analyzed from the *F. okeanokoites* genome BglII library in pUC13, six appeared to carry the fokIM gene. Three of these clones had a 8 kb BglII insert while the rest contained a 16 kb BglII fragment.

Plating efficiency of phage λ on these clones suggested that they also carried the fokIR gene. The clones with the 8-kb BglII insert appeared to be most resistant to phage infection. Furthermore, the FokI endonuclease activity was detected in the crude extract of this clone after partial purification on a phosphocellulose column. The plasmid, pUCfokIRM from this clone was chosen for further characterization.

The 5.5 kb PstI fragment was transferred to M13 phages and the nucleotide sequences of parts of this insert determined using Sanger's sequencing method (Sanger et al., *PNAS USA*, 74:5463–5467, 1977). The complete nucleotide sequence of the FokI RM system has been published by other laboratories (Looney et al., *Gene*, 80:193–208, 1989; Kita et al., *Nucleic Acid Res.*, 17:8741–8753, 1989; Kita et al., *J. Biol. Chem.* 264:5751–5756, 1989).

EXAMPLE II

Construction of an efficient overproducer clone of FokI endonuclease using polymerase chain reaction The PCR technique was used to alter transcriptional and translational signals surrounding the fokIR gene so as to achieve overexpression in *E. coli* (Skoglund et al., *Gene*, 88:1–5, 1990). The ribosome-binding site preceding the fokIR and fokIM genes were altered to match the consensus *E. coli* signal.

In the PCR reaction, plasmid pUCfokIRM DNA linearized with BamHI was used as the template. PCR reactions (100 μl) contained 0.25 nmol of each primer, 50 μM of each dNTP, 10 mM Tris.HCl (pH 8.3 at 25° C.), 50 mM KCl, 1.5 mM MgCl$_2$ 0.01% (W/V) gelatin, 1 ng of template DNA, 5 units of Taq DNA polymerase. The oligo primers used for the amplification of the fokIR and fokIM genes are shown in FIG. 1. Reaction mixtures (run in quadruplicate) were overlayed with mineral oil and reactions were carried out using Perkin-Elmer-Cetus Thermal Cycler.

Initial template denaturation was programmed for 2 min. Thereafter, the cycle profile was programmed as follows: 2 min at 37° C. (annealing), 5 min at 72° C. (extension), and 1 min at 94° C. (denaturation). This profile was repeated for 25 cycles and the final 72° C. extension was increased to 10 min. The aqueous layers of the reaction mixtures were pooled and extracted once with 1:1 phenol/chloroform and twice with chloroform. The DNA was ethanol-precipitated and resuspended in 20 μl TE buffer [10 mM Tris.HCl, (pH 7.5), 1 mM EDTA]. The DNA was then cleaved with appropriate restriction enzymes to generate cohesive ends and gel-purified.

Figure 2A:
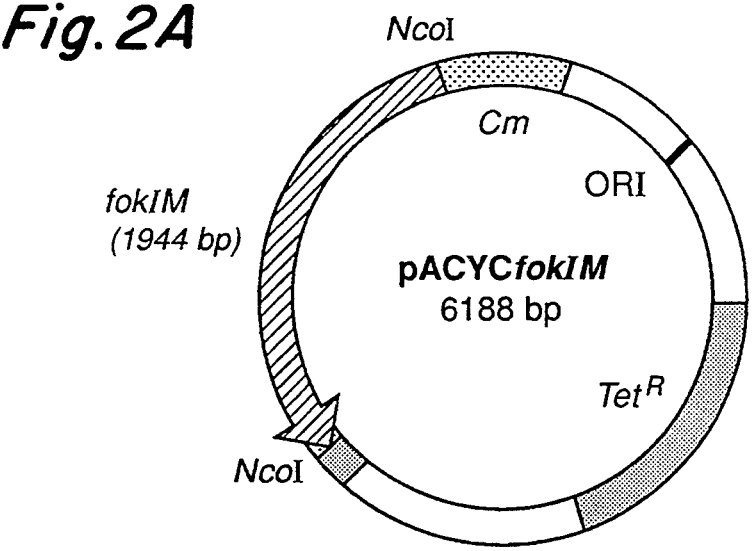
FIG. 2A, 2B and 2C shows the structure of plasmids pACYCfokIM, pRRSfokIR and pCBfokIR, respectively. The PCR-modified fokIM gene was inserted at the NcoI site of pACYC184 to form pACYCfokIM. The PCR-generated fokIR gene was inserted at the BamHI sites of pRRS and pCB to form pRRSfokIR and pCBfokIR, respectively. pRRS possesses a lac UV5 promoter and pCB contains a strong tac promoter. In addition, these vectors contain the positive retroregulator sequence downstream of the inserted fokIR gene.

The construction of an over-producer clone was done in two steps. First, the PCR-generated DNA containing the fokIM gene was digested with NcoI and gel purified. It was then ligated into NcoI-cleaved and dephosphorylated pACYC184 and the recombinant DNA transfected into *E. coli* RB791 i$^q$ or RR1 cells made competent as described by Maniatis et al (Maniatis et al., *Molecular Cloning. A laboratory manual* Cold Spring Harbor Laboratory, Cold Spring Harbor, N.Y., 1982). After Tc selection, several clones were picked and plasmid DNA was examined by restriction analysis for the presence of fokIM gene fragment in correct orientation to the chloramphenicol promoter of the vector (see FIG. 2A). This plasmid expresses FokI methylase constitutively and this protects the host from chromosomal cleavage, when the fokIR gene is introduced into the host on a compatible plasmid. The plasmid DNA from these clones are therefore resistant to FokI digestion.

Second, the PCR-generated fokIR fragment was ligated into BamHI-cleaved and dephosphorylated high expression vectors pRRS or pCB. pRRS possesses a lac UV5 promoter and pCB containing the strong tac promoter. In addition, these vectors contain the positive retroregulator stem-loop sequence derived from the crystal protein-encoding gene of *Bacillus Thuringiensis* downstream of the inserted fokIR gene. The recombinant DNA was transfected into competent *E. coli* RB791 i$^q$ [pACYCfokIM] or RR1[pACYCfokIM]cells. After Tc and Ap antibiotic selection, several clones were picked and plasmid DNA was examined by restriction analysis for fokIR gene fragment in correct orientation for expression from the vector promoters.

These constructs were then examined for enzyme production.

Figure 2B:
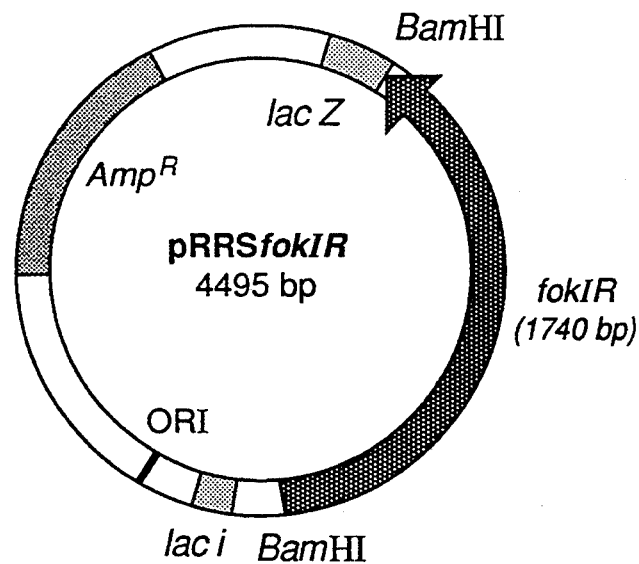
Figure 2C:
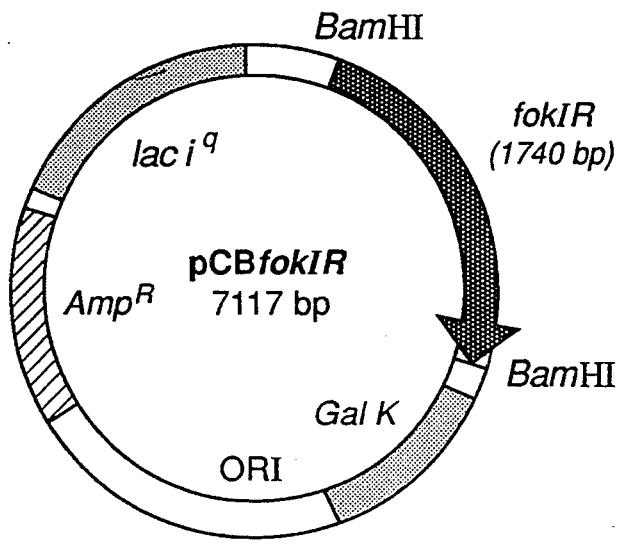

To produce the enzyme, plasmid-containing RB791 i9 or RR1 cells were grown at 37° C. with shaking in 2× concentrated TY medium [1.6% tryptone, 1% yeast extract, 0.5% NaCl (pH 7.2)] supplemented with 20 µg Tc/ml (except for the pUCfokIRM plasmid) and 50 µg Ap/ml. IPTG was added to a concentration of 1 mM when the cell density reached O.D.$_{600}$=0.8. The cells were incubated overnight (12 hr) with shaking. As is shown in FIGS. 2B and 2C, both constructs yield FokI to a level of 5–8% of the total cellular protein.

EXAMPLES III

Purification of FoKI endonuclease

A simple three-step purification procedure was used to obtain electrophoretically homogeneous FokI endonuclease. RR1 [pACYCfokIM, pRRSfokIR] were grown in 6L of 2×TY containing 20 µg Tc/ml and 50 µg/Ap ml at 37° C. to A$_{600}$=0.8. and then induced overnight with 1 mM IPTG. The cells were harvested by centrifugation and then resuspended in 250 ml of buffer A [10 mM Tris.phosphate (pH 8.0), 7 mM 2-mercaptoethanol, 1 mM EDTA, 10% glycerol] containing 50 mM NaCl.

The cells were disrupted at maximum intensity on a Branson Sonicator for 1 hr at 4° C. The sonicated cells were centrifuged at 12,000 g for 2 hr at 4° C. The supernatant was then diluted to 1L with buffer A containing 50 mM NaCl. The supernatant was loaded onto a 10 ml phosphocellulose (Whatman) column pre-equilibrated with buffer A containing 50 mM NaCl. The column was washed with 50 ml of loading buffer and the protein was eluted with a 80-ml total gradient of 0.05M to 0.5M NaCl in buffer A. The fractions were monitored by A$_{280}$ absorption and analyzed by electrophoresis on SDS (0.1%)-polyacrylamide (12%) gels (Laemmli, *Nature*, 222:680–685, 1970). Proteins were stained with coomassie blue.

Restriction endonuclease activity of the fractions were assayed using pTZ19R as substrate. The fractions containing FokI were pooled and fractionated with ammonium sulfate. The 50–70% ammonium sulfate fraction contained the FokI endonuclease. The precipitate was resuspended in 50 ml of buffer A containing 25 mM NaCl and loaded onto a DEAE column. FokI does not bind to DEAE while many contaminating proteins do. The flow-through was concentrated on a phosphocellulose column. Further purification was achieved using gel filtration (AcA 44) column. The FokI was purified to electrophoretic homogeneity using this procedure.

Figure 3:
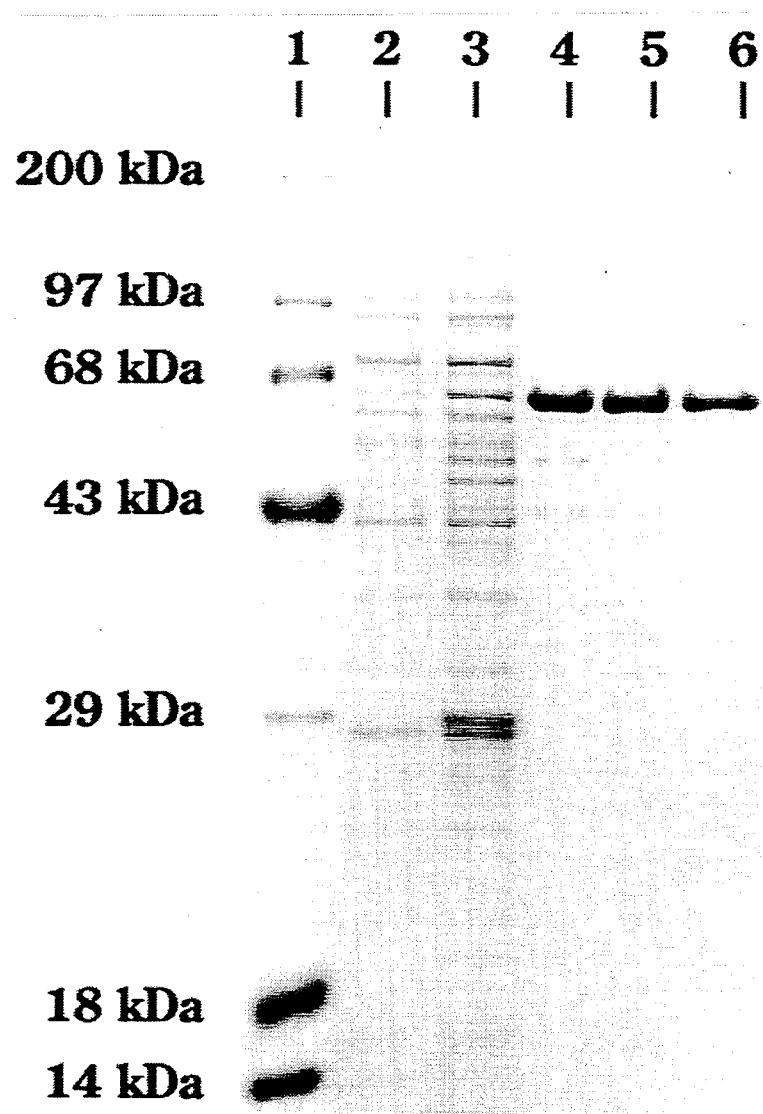
FIG. 3 shows SDS (0.1%)-polyacrylamide (12%) gel electrophoretic profiles at each step in the purification of FokI endonuclease. Lanes: 1, protein standards; 2, crude extract from uninduced cells; 3, crude extract from cells induced with 1 mM IPTG; 4, phosphocellulose pool; 5, 50-70% $(NH_4)_2SO_4$, fractionation pool; and 6, DEAE pool.

SDS (0.1%) polyacrylamide (12%) gel electrophoresis profiles of protein species present at each stage of purification are shown in FIG. 3. The sequence of the first ten amino acids of the purified enzyme was determined by protein sequencing. The determined sequence was the same as that predicted from the nucleotide sequence. Crystals of this purified enzyme have also been grown using PEG 4000 as the precipitant. FokI endonuclease was purified further using AcA44 gel filtration column.

EXAMPLE IV

Analysis of FokIR endonuclease by trypsin cleavage in the presence of DNA substrate Trypsin is a serine protease and it cleaves at the C-terminal side of lysine and arginine residues. This is a very useful enzyme to study the domain structure of proteins and enzymes. Trypsin digestion of FokI in the presence of its substrate, d-5'-CCTCTGGATGCTCTC-3'(SEQ ID NO: 10): 5'-GAGAGCATCCAGAGG-3'(SEQ ID NO: 11) was carried out with an oligonucleotide duplex to FokI molar ratio of 2.5:1. FokI (200 µg) was incubated with the oligonucleotide duplex in a volume 180 µl containing 10 mM Tris.HCl, 50 mM NaCl, 10% glycerol and 10 mM MgCl$_2$ at RT for 1 hr. Trypsin (20 µl, 0.2 mg/ml) was added to the mixture. Aliquots (28 µl) from the reaction mixture were removed at different time intervals and quenched with excess trypsin inhibitor, antipain. The tryptic fragments were purified by reversed-phase HPLC and their N-terminus sequence determined using an automatic protein sequenator from Applied Biosystems.

Figure 4:
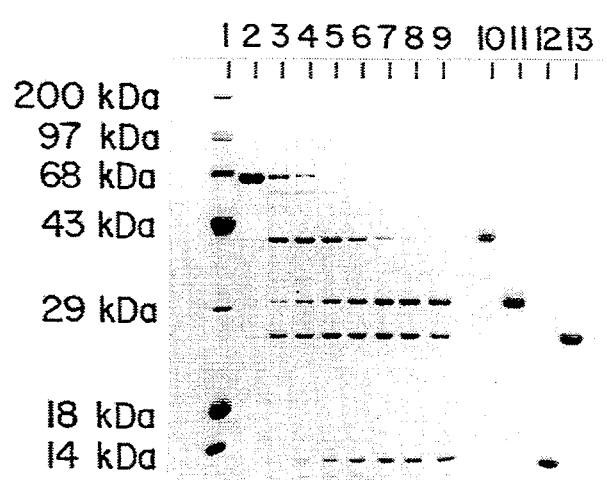
FIG. 4 shows SDS (0.1%)-polyacrylamide (12%) gel electrophoretic profiles of tryptic fragments at various time points of trypsin digestion of FokI endonuclease in presence of the oligonucleotide DNA substrate, d-5'-CCTCTGGATGCTCTC-3'(SEQ ID NO: 10): 5'-

The time course of trypsin digestion of FokI endonuclease in the presence of 2.5 molar excess of oligonucleotide substrate and 10 mM MgCl$_2$ is shown in FIG. 4. At the 2.5 min time point only two major fragments other than the intact FokI were present, a 41 kDa fragment and a 25 kDa fragment. Upon further trypsin digestion, the 41 kDa fragment degraded into a 30 kDa fragment and 11 kDA fragment. The 25 kDa fragment appeared to be resistant to any further trypsin digestion. This fragment appeared to be less stable if the trypsin digestion of FokI-oligo complex was carried out in the absence of MgCl$_2$.

Only three major fragments (30 kDa, 25 kDa and 11 kDa) were present at the 160 min time point. Each of these fragments (41 kDa, 30 kDa, 25 kDa and 11 kDa) was purified by reversed-phase HPLC and their N-terminal amino acid sequence were determined (Table I). By comparing these N-terminal sequences to the predicted sequence of FokI, the 41 kDa and 25 kDa fragments were identified as N-terminal and C-terminal fragments, respectively. In addition, the 30 kDa fragment was N-terminal.

EXAMPLE V

Isolation of DNA binding tryptic fragments of FokI endonuclease using oligo dT-cellulose affinity column The DNA binding properties of the tryptic fragments were analyzed using an oligo dT-cellulose column. FokI (160 µg) was incubated with the 2.5 molar excess oligonucleotide duplex [d-5'-CCTCTGGATGCTCTC(A)$_{15}$-3'(SEQ ID NO: 14): 5'GAGAGCATCCAGAGG(A)$_{15}$-3'(SEQ ID NO: 15)] in a volume of 90 µl containing 10 mM Tris.HCl (pH 8), 50 mM NaCl, 10% glycerol and 10 mM MgCl$_2$ at RT for 1 hr. Trypsin (10 µl, 0.2 mg/ml) was added to the solution to initiate digestion. The ratio of trypsin to FokI (by weight) was 1:80. Digestion was carried out for 10 min to obtain predominantly 41 kDa N-terminal fragment and 25 kDa C-terminal fragments in the reaction mixture. The reaction was quenched with large excess of antipain (10 µg) and diluted in loading buffer [10 mM.Tris HCl (pH 8.0), 1 mM EDTA and 100 mM MgCl$_2$] to a final volume of 400 µl.

The solution was loaded onto a oligo dT-cellulose column (0.5 ml, Sigma, catalog #0-7751) pre-equilibrated with the loading buffer. The breakthrough was passed over the oligo dT-cellulose column six times. The column was washed with 5 ml of loading buffer and then eluted twice with 0.4 ml of 10 mM Tris.HCl (pH 8.0), 1 mM EDTA. These fractions contained the tryptic fragments that were bound to the oligonucleotide DNA substrate. The tryptic fragment bound to the oligo dT-cellulose column was analyzed by SDS-polyacrylamide gel electrophoresis.

In a separate reaction, the trypsin digestion was carried out for 160 min to obtain predominantly the 30 kDa, 25 kDa and 11 kDa fragments in the reaction mixture.

Trypsin digestion of FokI endonuclease for 10 min yielded the 41 kDa N-terminal fragment and 25 kDa C-terminal fragments as the predominant species in the reaction mixture (FIG. 5, Lane 3). When this mixture was passed over the oligo dT-cellulose column, only the 41 kDa N-terminal fragment is retained by the column suggesting that the DNA binding property of FokI endonuclease is in the N-terminal ⅔'s of the enzyme. The 25 kDa fragment is not retained by the oligo dT-cellulose column.

Trypsin digestion of FokI-oligo complex for 160 min yielded predominantly the 30 kDa, 25 kDa and 11 kDa fragments (FIG. 5, Lane 5). When this reaction mixture was passed over oligo dT-cellulose column, only the 30 kDa and 11 kDa fragments were retained. It appears these species together bind DNA and they arise from further degradation of 41 kDa N-terminal fragment. The 25 kDa fragment was not retained by oligo dT-cellulose column. It also did not bind to DEAE and thus could be purified by passage through a DEAE column and recovering it in the breakthrough volume.

FokI (390 μg) was incubated with 2.5 molar excess of oligonucleotide duplex [d-5'-CCTCTGGATGCTCTC-3 (SEQ ID NO: 10)':5'-GAGAGCATCCAGAGG-3'(SEQ ID NO: 11)] in a total volume of 170 μl containing 10 mM Tris.HCl (pH 8), 50 mM NaCl and 10% glycerol at RT for 1 hr. Digestion with trypsin (30 μl; 0.2 mg/ml) in the absence of $MgCl_2$ was for 10 min at RT to maximize the yield of the 41 kDa N-terminal fragment. The reaction was quenched with excess antipain (200 μl). The tryptic digest was passed through a DEAE column. The 25 kDa of C-terminal fragment was recovered in the breakthrough volume. All the other tryptic fragments (41 kDa, 30 kDa and 11 kDa) were retained by the column and were eluted with 0.5M NaCl buffer (3×200 μl). In a separate experiment, the trypsin digestion of FokI-oligo complex was done in presence of 10 mM $MgCl_2$ at RT for 60 min to maximize the yield of 30 kDa and 11 kDa fragments. This purified fragment cleaved non-specifically both unmethylated DNA substrate (pTZ19R; FIG. 6) and methylated DNA substrate (pACYCfokIM) in the presence of $MgCl_2$. These products are small, indicating that it is relatively non-specific in cleavage. The products were dephosphorylated using calf intestinal phosphatase and rephosphorylated using polynucleotide kinase and [γ-$^{32}$P] ATP. The $^{32}$P-labeled products were digested to mononucleotides using DNase I and snake venom phosphodiesterase. Analysis of the mononucleotides by PEI-cellulose chromatography indicates that the 25 kDa fragment cleaved preferentially phosphodiester bonds 5' to G>A>>T~C. The 25 kDa C-terminal fragment thus constitutes the cleavage domain of FokI endonuclease.

The 41 kDa N-terminal fragment-oligo complex was purified by agarose gel electrophoresis. FokI endonuclease (200 μg) was incubated with 2.5 molar excess of oligonucleotide duplex, [d-5'-CCTCTGGATGCTCTC-3'(SEQ ID NO: 10): 5'-GAGAGCATCCAGAGG-3'(SEQ ID NO:11)] in a volume of 180 μl containing 10 mM Tris.HCl (pH 8.0), 50 mM NaCl and 10% glycerol at RT for 1 hr. Tracer amounts of $^{32}$P-labeled oligonucleotide duplex was incorporated into the complex to monitor it during gel electrophoresis. Digestion with trypsin (20 μl; 0.2 mg/ml) was for 12 min at RT to maximize the yield of the 41 kDa N-terminal fragment. The reaction was quenched with excess antipain. The 41 kDa N-terminal fragment-oligo complex was purified by agarose gel electrophoresis. The band corresponding to the complex was excised and recovered by electroelution in a dialysis bag (~600 μl). Analysis of the complex by SDS-PAGE revealed 41 kDa N-terminal fragment to be the major component. The 30 kDa N-terminal fragment and the 11 kDa C-terminal fragment were present as minor components. These together appeared to bind DNA and co-migrate with the 41 kDa N-terminal fragment-oligo complex.

The binding specificity of the 41 KDa N-terminal fragment was determined using gel mobility shift assays.

EXAMPLE VI

Gel Mobility shift assays

The specific oligos (d-5'-CCTCTGGATGCTCTC-3'(SEQ ID NO: 10) and d-5'-GAGAGCATCCAGAGG-3'(SEQ ID NO: 11)) were 5'-$^{32}$P-labeled in a reaction mixture of 25 μl containing 40 mM Tris.HCl(pH7.5), 20 mM $MgCl_2$, 50 mM NaCl, 10 mM DTT, 10 units of T4 polynucleotide kinase (from New England Biolabs) and 20 μCi[γ-$^{32}$P] ATP (3000 Ci/mmol). The mixture was incubated at 37° C. for 30 min. The kinase was inactivated by heating the reaction mixture to 70° C. for 15 min. After addition of 200 μl of water, the solution was passed through Sephadex G-25 (Superfine) column (Pharmacia) to remove the unreacted [γ-$^{32}$P] ATP. The final concentration of labeled single-strand oligos were 27 μM.

The single-strands were then annealed to form the duplex in 10 mM Tris.HCl (pH 8.0), 50 mM NaCl to a concentration of 12 μM. 1 μl of the solution contained ~12 picomoles of oligo duplex and ~50×10$^3$ cpm. The non-specific oligos (d-5'-TAATTGATTCTTAA-3'(SEQ ID NO: 12) and d-5'-ATTAAGAATCAATT-3'(SEQ ID NO:13)) were labeled with [γ-$^{32}$P] ATP and polynucleotide kinase as described herein. The single-stranded oligos were annealed to yield the duplex at a concentration of 12 μM. 1 μl of the solution contained ~12 picomoles of oligo duplex and ~25×10$^3$ cpm. The non-specific oligos (d-5'-TAATTGATTCTTAA-3'(SEQ ID NO: 12) and d-5'-ATTAAGAATCAATT-3'(SEQ ID NO: 13)) were labeled with [γ-$^{32}$P] ATP and polynucleotide Kinase as described herein. The single-strand oligos were annealed to yield the duplex at a concentration of 12 MM. 1 μl of the solution contained 42 picomoles of oligo duplex and ~25×10$^3$ cpm.

10 μl of 41 kDa N-terminal fragment-oligo complex (~2 pmoles) in 10 mM Tris.HCl, 50 mM NaCl and 10 mM $MgCl_2$ was incubated with 1 μl of $^{32}$P-labeled specific oligonucleotide duplex (or $^{32}$P-labeled nonspecific oligonucleotide duplex) at 37° C. for 30 min and 120 min respectively. 5 μl of 75% glycerol was added to each sample and loaded on a 8% nondenaturing polyacrylamide gel. Electrophoresis was at 300 volts in TBE buffer till bromophenol blue moved ~6 cm from the top of the gel. The gel was dried and autoradiographed.

The complex readily exchanged $^{32}$P-labeled specific oligonucleotide duplex that contained the FokI recognition site as seen from the gel mobility shift assays (FIG. 7). It did not, however, exchange the $^{32}$P-labeled non-specific oligonucleotide duplex that did not contain the FokI recognition site. These results indicate that all the information necessary for sequence-specific recognition of DNA are encoded within the 41 kDa N-terminal fragment of FokI.

EXAMPLE VII

Analysis of FokI by trypsin cleavage in the absence of DNA substrate

A time course of trypsin digestion of FokI endonuclease in the absence of the DNA substrate is shown in FIG. 8. Initially, FokI cleaved into a 58 kDa fragment and a 8 kDa fragment. The 58 kDa fragment did not bind DNA substrates and is not retained by the oligo dT-cellulose column. On further digestion, the 58 kDa fragment degraded into several intermediate tryptic fragments. However, the complete trypsin digestion yielded only 25 kDa fragments (appears as two overlapping bands).

Each of these species (58 kDa, 25 kDa and 8 kDa) were purified by reversed phase HPLC and their amino terminal amino acid sequence determined (Table I). Comparison of the N-terminal sequences to the predicted FokI sequence revealed the 8 kDa fragment to be N-terminal and the 58 kDa fragment to be C-terminal. This further supports the conclusion that N-terminus of FokI is responsible for the recognition domain. Sequencing the N-terminus of the 25 kDa fragments revealed the presence of two different components. A time course of trypsin digestion of FokI endonuclease in the presence of a non-specific DNA substrate yielded a profile similar to the one obtained when trypsin digestion of FokI is carried out in absence of any DNA substrate.

EXAMPLE VIII

Cleavage specificity of the 25 kDa C-terminal tryptic fragment of FokI

The 25 kDa C-terminal tryptic fragment of FokI cleaved pTZ19R to small products indicating non-specific cleavage. The degradation products were dephosphorylated by calf intestinal phosphatase and $^{32}$P-labeled with the polynucleotide kinase and [$\tau$-$^{32}$P] ATP. The excess label was removed using a Sephadex G-25 (Superfine) column. The labeled products were then digested with 1 unit of pancreatic DNase I (Boehringer-Mannheim) in buffer containing 50 mM Tris.HCl(pH7.6), 10mM MgCl$_2$ at 37° C. for 1 hr. Then, 0.02 units of snake venom phosphodiesterase was added to the reaction mixture and digested at 37° C. for 1 hr.

EXAMPLE IX

Functional domains in FokI restriction endonuclease

Analysis of functional domains of FokI (in the presence and absence of substrates) using trypsin was summarized in FIGS. 9A and 9B. Binding of DNA substrate by FokI was accompanied by alteration in the structure of the enzyme. This study supports the presence of two separate protein domains within this enzyme: one for sequence-specific recognition and the other for endonuclease activity. The results indicate that the recognition domain is at the N-terminus of the FokI endonuclease, while the cleavage domain is probably in the C-terminus third of the molecule.

TABLE 1

| | Amino-terminal sequences of FokI fragments from trypsin digestion | | |
|---|---|---|---|
| Fragment | Amino-terminal sequence | DNA substrate | SEQ ID NO |
| 8 kDa | VSKIRTFG*VQNPGKFENLKRVVQVFDRS | — | 16 |
| 58 kDa | SEAPCDAIIQ | | 17 |
| 25 kDa | QLVKSELEEK | + | 18 |
| 41 kDa | VSKIRTFGWV | | 19 |
| 30 kDa | VSKIRTFGWV | | 19 |
| 11 kDa | FTRVPKRVY | | 20 |

TABLE 2

| No. (1) | ENase-IIS$^a$ (isoschizomers) (2) | Protruding ends$^e$ (5) | Species (strain)$^d$ (6) | Co-produced ENases$^c$ (7) | Described MTases-II$^f$ [C or A] (8) | Commercial availability$^g$ (9) | References (10) |
|---|---|---|---|---|---|---|---|
| 1. | AlwI (BinI) (BthII)$^i$ | 5'N$_1$ | Acinetobacter lwofii | | | N, Z | Mo2, Ne3 |
| 2. | AlwXI (Bbvi) | 5'N$_4$ | Acinetobacter lwofii X | | (M.BbvI) [C-5] | | Mo6 |
| 3. | Alw26I (BsmAI) | 5'N$_4$ | Acinetobacter lwofii RFL26 | | M.Alw26I [C-5 and A-N6] | | G11, Bi2 |
| 4. | BbsI (BbvII) | 5'N$_4$ | Bacillus brevis (laterosporus NEB573) | | | N | Mo2, Ne3 |
| 5. | BbvI (AlwXI) (Uball09I)$_i$ (Bsp432I) | 5'N$_4$$_4$ | Bacillus brevis (ATCC 9999) | BbvII | M.BbvI [C-5] | G, I, N, Z | Ba4, Do1, Do2, Gi2, Gi3, Ha4, Ha5, Ne3, Sc2, Val |
| 6. | BbvII (Bbv16I)$^i$ (BspVI)$^i$ | 5'N$_4$ | Bacillus brevis 80 | BbvI | | | Bu1, Bu2, Do2, Ma4 |
| 7. | BcefI | 5'N$_1$ | Bacillus cereus subsp. flourescens | | | | Ve1, Ve2 |
| 8. | BccI | | Bacteroides caccae | | (N) | | Mo2 |

TABLE 2-continued

| No. (1) | ENase-IIS[a] (isoschizomers) (2) | Protruding ends[c] (5) | Species (strain)[d] (6) | Co-produced ENases[e] (7) | Described MTases-II[f] [C or A] (8) | Commercial availability[g] (9) | References (10) |
|---|---|---|---|---|---|---|---|
| 9. | BcgI | 3'N$_2$ 3'N$_2$ | *Bacillus coagulans* (NEB 566) | | | N | H. Kong, No3 |
| 10. | BinI (AlwI) (BthII)[i] | 5'N$_1$ | *Bifidobacterium infantis* | | | N | Bo2, Kh1, Kh2 |
| 11. | BsaI (Eco31I)[j] | 5'N$_4$ | *Bacillus stearothermophilus* 6-55 | | | N | H. Kong, No2, Ne3 |
| 12. | BsgI | 3'N$_2$ | *Bacilus sphaericus* GC | | | N | Sc2 |
| 13. | BsmAI (Alw26I) | 5'N$_4$ | *Bacillus stearothermophilus* A664 (NEB 481) | | | N | Ch1, Ko1, Ne3 |
| 14. | BspMI | 5'N$_4$ | *Bacillus* species M (NEB 356) | BspMII | | N | Ha1, Ki2, Ki4, Ku1, Mc2, Mo2, Mo4, Mo7 Ne3 |
| 15. | EarI (Ksp632I) | 5'N$_3$ | *Enterobacter aerogenes* (NEB 450) | | | N | Ne3, Po3 |
| 16. | Eco31I (BsaI)[j] | 5'N$_4$ | *Escherichia coli* RFL31 | | M.Eco31I [C-5] and [A-N6] | F | Bi2, Bu3 |
| 17. | Eco57I (Bsp6II)[i] (Eco112I)[i] (Eco125I)[i] (FsfI)[i] | 3'N$_2$ | *Escherichia coli* RFL57$_1$ | | M.Eco57I [A-N6] | F, N | Ja2, Ja3, Pe1, Pe2 |
| 18. | Esp3I | 5'N$_4$ | Erwinia sp RFL3 | | M.Esp3I [C-5, A-N6] | F, N | Bi2 |
| 19. | FauI | 5'N$_2$ | *Flavobacterium aquatili* | | | | De1 |
| 20. | FokI (HinGuII) | 5'N$_4$ | *Flavobacterium okeanokoites* | | M.FokI [A-N6] | A, M, N, S, U, Z | Ba4, Ha2, Ha3, Ka1, Ka2, Ki1, Ki3, Ki4, Ki5, Ki6, Ki7, Kr1, La1, Lo1, Lu1, Ma1, Ma3, Mc1, Ne3, Nw1, Po1, Po4, Po5, P06, Sc3, Sc4, Sk1, Su2, Su3, Su4, Sz1, Ve3, Ve4, Wi1 |
| 21. | GsuI (Bco35I)[i] (Bsp22I)[i] (Bsp28I)[i] | 3'N$_2$ | *Gluconobacter dioxyacetonicus* H-15T | | M.GsuI | F, N | Bi1, Ja1, Pe1, Pe2 |
| 22. | HgaI | 5'N$_5$ | *Haemophilus gallinarum* (ATCC14385) | | M.HgaI (two MTases) [C-5] | N, Z | Ba4, Br1, Br6, Ko4, Kr1, No8, Ne1, Ne3, Su1, Ta1, To1, Ur1 Na2 |
| 23. | HinGuII (FokI) | 5'N$_4$ | *Haemophilus infuenzae* GU | | | | |
| 24. | HphI (NgoVII) (NgoBI)[i] | 3'N$_i$ (or blunt) | *Haemophilus parahaemolyticus* | | M.HphI [A-N6] | N, Z | Ba1, Co1, Kl1, Ne2, Ne3, Ro1 |
| 25. | Ksp632I (EarI) (BsrEI)[i] | 5'N$_3$ | *Kluyvera* sp. 632 | | | M | Bo1 |
| 26. | MboII (NcuI)[i] (TceI)[i] | 3'N$_1$ | *Moraxella bovis* (ATCC10900) | MboI | M.MboII [A-N6] | B, G, I, N, P, U, Z | Ba1, Br3, Br5, En1, Ga1, Ge1, Ha2, Mc1, Mc3, Na1, Na2, Ne2, Ne3, Sc1, Se1, Sm1 |
| 27. | MmeI | 3'N$_2$ | *Methylophilus methyltrophus* | MmeII | | U | Bo3, Tu1 |
| 28. | MnlI | 3'N$_1$ | *Moraxella nonliquefaciens* (ATCC17953) | | | I, N, S, Z | Br2, Ne3, Sc2, Vi1, Ea1 |
| 29. | NgoVIII (HphI) | n.d. | *Neisseria gonorrhoeae* | | M.NgoVIII | | Ko2 |
| 30. | PleI | 5'N$_1$ | *Pseudomonas lemoignei* (NEB418) | | | N | Mo6, Ne3 |
| 31. | RleAI | 3'N$_3$ | *Rhizobium leguminosarum* | | | | Ve5 |
| 32. | SapI | 5'N$_3$ | *Saccharopolyspora* sp. | | | N | Mo2, Ne3 |
| 33. | SfaNI (BscAI)[i] | 5'N$_4$ | *Streptococcus faecalis* ND547 | | M.SfaI | N, Z | Ba4, Ne3, Po5, Po6, Sc2, Sc3, Sc5, Sp1 |
| 34. | TaqII | 3'N$_2$ | *Thermus aquaticus* | TaqI | | U | Ba2, My1 |

TABLE 2-continued

| No. (1) | ENase-IIS[a] (isoschi-zomers) (2) | Protruding ends[c] (5) | Species (strain)[d] (6) | Co-produced ENases[e] (7) | Described MTases-II[f] [C or A] (8) | Commercial availability[g] (9) | References (10) |
|---|---|---|---|---|---|---|---|
| 35. | Tth111II | 3'N$_2$ | *Thermus thermophilus* 111 | Tth111I | | Y, Z | Sh1, Sh2 |
| 36. | Sts I | | *Streptococcus sanguis* 54 | | | | |
| Related ENases:[h] | | | | | | | |
| 36. | BsmI (Asp35HI)[k] | 3'N$_1$ | *Bacillus stero-thermophilus* NUB36 | | | N | Gil, Ha6, In1, M07, My1, Ne3, Pa1 |
| 37. | BarI (BarSI) | 3'N$_1$ | *Bacillus stearo-thermophilus* (NEB447) | | | N | Ne3, Po2 |

[a]Class-II restriction endonucleases (ENases-IIS) as listed (Ke1: Ro2). Isoschizomers are listed in parentheses (very recently discovered or incompletely characterized isoschizomers are in footnotes i–k). An ENase-IIS is defined as an enzyme which cuts at precise distance away from its recognition site, without cleaving this site. Enzymes in lines 36 and 37 (BsmI, Bsr, six Asp, and BscCI) do not fit this definition because one of the two cuts is within the recognition site, but they were included because several of their properties and applications are qyite similar to those of enzymes 1–35. ENase in line 29 (NgoVII) was not described, but the M.Ngo VIII MTase appears to match the HphI). Genes coding for Eco571 and FokI were cloned (Ja3; Wi1). ENases BcgI, Eco571 and GsuI (and their isoschizomers?) require or are stimulated by AdoMet.
[b]The recognition sequences are asymmetric [with exception of those marked S (in bp column) which display a partial symmetry (which might be incidental)], and are oriented so that the cut sites are to the right (downstream) of them.
E.g., GGATC(N)$_4$ (line 1), indicates that the cut on the upper strand is between 4th and 5th nt beyond C;
   CCTAG(N)$_5$
on the lower strand the cut is between 5th and 6th nt beyond G. Length of the recognition site is giv en in bp, and the symbols + or − below it indicate whether the purified enzyme cuts (+) or does not cut (−) ss DNA. N, A, or C or G or T; R, A or G, C or T.
[c]As deduced from cut sites (see column 3). n.d., not determined.
[d]Strains which produce the specified ENases-IIS.
[e]Other unrelated ENases produced by the same strain.
[f]MTases-IIS isolated from the same strain. Genes bbvIM, eco57IM, fokIM, hgaIM, mboIIM and sfaNIM (coding for M.BbvI, M.Eco57I, M.FokI, M.HgaI, M.MboII, and M.SfaNI, respectively; Sz3) were cloned (Ba4; Bo0; Ja3; Wi1). MTases with the same site specificity, but produced by another strain, are in parentheseses. Methylated based (m$^5$C or mN$^6$A) are shown in brackets (as C-5 or A-N6, respectively).
[g]A, Amersham Buchler, Buckinghamshire (U.K.); B, BRL/Life Technologies, Gaithersburg, MD; F, ESP Fermentas, 2328 Vilnius, Lithuania (U.S.S.R.) (some also available from N); G, Anglian Biotechnology, Colchester (U.K.); 1, IBI/International Biotechnology, New Haven, CT; M, Boehringer/Mannheim, Mannheim (F.R.G.); N, New England Biolabs, Beverly, MA; P, PL-Pharmacia, Milwaukee, WI; S, Stratagene, La Jolla, Ca; U, Dept of Microbology, University of Gdansk, Gdansk (Poland); Y, NY Biolabs, New York, NY; Z, see American Chemical Society Biotech buyers' Guide (1991). Parentheses indicate that the ENase is produced, but not yet commercially available.
[h]These enzymes do not formally belong to class IIS (see footnotes). They are also designated IIT (Kel); (N)$_{-1}$ indicates a cut within the recognition site in the lower strand (see arrowhead).
[i]Cuts unknown (See Ro2).
[j]Also 28 additional ENases: Cfr561, Eco42, Eco51I, Eco95I, Eco97I, Eco 10I, Eco 120I, Eco 127I, Eco129I, Eco155I, Eco 156I, Eco 157I, Eco 162I, 185I, Eco 191I, Eco 203I, Eco 205I, Eco 217I, Eco 225I, Eco 239I, Eco 240I, Eco 241I, Eco 246I, Eco 247I, PpaI, Sau 12I, which have the same recognition sequence, but for most of them cuts are unknown (see Ro2). PpaI has the same cuts as Eco 31I (Ne3).
[k]also additional isochizomers Asp26HI, Asp27HI, Asp36HI, Asp40HI, Asp50HI (Ro2), and BscCI (from Bacillus sp. 2G).
from Szybalski et al. [Gene 100:14-26 (1991)]

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
      ( A ) LENGTH: 5 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:1:

GGATG 5

( 2 ) INFORMATION FOR SEQ ID NO:2:

( i ) SEQUENCE CHARACTERISTICS:
      ( A ) LENGTH: 5 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:2:

CATCC 5

( 2 ) INFORMATION FOR SEQ ID NO:3:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 20..37

( x i ) SEQUENCE DESCRIPTION: SEQ ID NO:3:

TACCATGGAG GTTTAAAAT ATG AGA TTT ATT GGC AGC    37
        Met Arg Phe Ile Gly Ser
        1      5

( 2 ) INFORMATION FOR SEQ ID NO:4:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

Met Arg Phe Ile Gly Ser
1     5

( 2 ) INFORMATION FOR SEQ ID NO:5:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

ATACCATGGG AATTAAATGA CACAGCATCA    30

( 2 ) INFORMATION FOR SEQ ID NO:6:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 22..42

( x i ) SEQUENCE DESCRIPTION: SEQ ID NO:6:

TAGGATCCGG AGGTTTAAAA T ATG GTT TCT AAA ATA AGA ACT    42
        Met Val Ser Lys Ile Arg Thr
        1      5

( 2 ) INFORMATION FOR SEQ ID NO:7:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

Met Val Ser Lys Ile Arg Thr
1               5

( 2 ) INFORMATION FOR SEQ ID NO:8:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TAGGATCCTC ATTAAAAGTT TATCTCGCCG TTATT    35

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

Asn Asn Gly Glu Ile Asn Phe
1               5

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CCTCTGGATG CTCTC    15

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GAGAGCATCC AGAGG    15

( 2 ) INFORMATION FOR SEQ ID NO:12:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

TAATTGATTC TTAA    14

( 2 ) INFORMATION FOR SEQ ID NO:13:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

ATTAAGAATC AATT        14

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CCTCTGGATG CTCTCAAAAA AAAAAAAAAA        30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GAGAGCATCC AGAGGAAAAA AAAAAAAAAA        30

( 2 ) INFORMATION FOR SEQ ID NO:16:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Val Ser Lys Ile Arg Thr Phe Gly Xaa Val Gln Asn Pro Gly Lys Phe
1              5                    10              15

Glu Asn Leu Lys Arg Val Val Gln Val Phe Asp Arg Ser
            20                    25

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Ser Glu Ala Pro Cys Asp Ala Ile Ile Gln
1              5                    10

(2) INFORMATION FOR SEQ ID NO:18:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:18:

Gln Leu Val Lys Ser Glu Leu Glu Glu Lys
  1               5                   10

(2) INFORMATION FOR SEQ ID NO:19:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:19:

Val Ser Lys Ile Arg Thr Phe Gly Trp Val
  1               5                   10

(2) INFORMATION FOR SEQ ID NO:20:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:20:

Phe Thr Arg Val Pro Lys Arg Val Tyr
  1               5

All publications mentioned hereinabove are hereby incorporated by reference.

While the foregoing invention has been described in some detail for purposes of clarity and understanding, it will be appreciated by one skilled in the art that various changes in form and detail can be made without departing from the true scope of the invention.

What is claimed is:

1. An isolated DNA segment encoding the N-terminus of a Type IIS endonuclease which contains the sequence-specific recognition activity of said Type IIS endonuclease, said Type IIS endonuclease being FokI restriction endonuclease and said N-terminus having a molecular weight of about 41 kilodaltons as determined by SDS-polyacrylamide gel electrophoresis wherein said isolated DNA segment encodes amino acids 1–382 of said FokI restriction endonuclease.

2. An isolated DNA segment encoding the C-terminus of a Type IIS endonuclease which contains the cleavage activity of said Type IIS endonuclease, said Type IIS endonuclease being FokI and said C-terminus having a molecular weight of about 25 kilodaltons, as determined by SDS-polyacrylamide gel electrophoresis, wherein said isolated DNA segment encodes amino acids 383–578 of said FokI restriction endonuclease.

3. An isolated DNA segment encoding the N-terminus of a Type IIS endonuclease which contains the sequence-specific recognition activity of said Type IIS endonuclease, said Type IIS endonuclease being FokI restriction endonuclease and having a molecular weight of about 41 kilodaltons as measured by SDS-polyacrylamide gel electrophoresis.

4. An isolated DNA segment encoding the C-terminus of a Type IIS endonuclease which contains the cleavage activity of said Type IIS endonuclease, said Type IIS endonuclease being FokI restriction endonuclease and having a molecular weight of about 25 kilodaltons as determined by SDS-polyacrylamide gel electrophoresis.

5. An isolated protein consisting essentially of the N-terminus of the FokI restriction endonuclease which protein has the sequence-specific recognition activity of said endonuclease and which protein is amino acids 1–382 of said FokI restriction endonuclease.

6. An isolated protein consisting essentially of the C-terminus of the FokI restriction endonuclease which protein has the cleavage activity of said endonuclease and which protein is amino acids 383–578 of said FokI restriction endonuclease.

* * * * *

UNITED STATES PATENT AND TRADEMARK OFFICE
CERTIFICATE OF CORRECTION

PATENT NO. : 5,356,802

DATED : October 18, 1994

INVENTOR(S) : CHANDRASEGARAN

It is certified that error appears in the above-identified patent and that said Letters Patent is hereby corrected as shown below:

Column 1, line 5
Prior to the specification, insert the following:

--This patent application was supported in part by grant GM 42140 from the National Institutes of Health. The government has certain rights in the invention.--

Signed and Sealed this

Fourth Day of July, 1995

Attest:

BRUCE LEHMAN

Attesting Officer

Commissioner of Patents and Trademarks